US011298855B2

(12) United States Patent
Kweon et al.

(10) Patent No.: US 11,298,855 B2
(45) Date of Patent: Apr. 12, 2022

(54) METHOD FOR MANUFACTURING HYALURONATE FILM, AND HYALURONATE FILM MANUFACTURED THEREBY

(71) Applicant: JINWOO BIO CO., LTD., Seoul (KR)

(72) Inventors: Dong Keon Kweon, Yongin-si (KR); Joo Yeon Hong, Guri-si (KR); Ji Hyun Bang, Anyang-si (KR); Seung Taik Lim, Seoul (KR); So Mang Choi, Seongnam-si (KR); Seul Ki Kim, Seoul (KR); Man Ha, Seoul (KR); Young Mo Lee, Seoul (KR)

(73) Assignee: JINWOO BIO CO., LTD., Seoul (KR)

( * ) Notice: Subject to any disclaimer, the term of this patent is extended or adjusted under 35 U.S.C. 154(b) by 133 days.

(21) Appl. No.: 16/491,054

(22) PCT Filed: Mar. 7, 2018

(86) PCT No.: PCT/KR2018/002727
§ 371 (c)(1),
(2) Date: Sep. 4, 2019

(87) PCT Pub. No.: WO2018/164489
PCT Pub. Date: Sep. 13, 2018

(65) Prior Publication Data
US 2020/0016795 A1   Jan. 16, 2020

(30) Foreign Application Priority Data

Mar. 7, 2017 (KR) .................. 10-2017-0029094
Sep. 27, 2017 (KR) .................. 10-2017-0125213

(51) Int. Cl.
*B29C 39/24* (2006.01)
*B29C 39/42* (2006.01)
(Continued)

(52) U.S. Cl.
CPC ............ *B29C 39/003* (2013.01); *B29C 39/24* (2013.01); *B29C 39/42* (2013.01); *C08L 5/08* (2013.01);
(Continued)

(58) Field of Classification Search
None
See application file for complete search history.

(56) References Cited

U.S. PATENT DOCUMENTS 6,630,167 B2   10/2003   Zhang

FOREIGN PATENT DOCUMENTS

CN   102504297 A   6/2012
EP   0193510 A1   9/1986
(Continued)

OTHER PUBLICATIONS

JP-2014114355 (Takeshi) Dec. 2012 (online machine translation), [Retrieved on Apr. 12, 2021]. Retrieved from: Espacenet (Year: 2012).*
(Continued)

*Primary Examiner* — Kelly M Gambetta
*Assistant Examiner* — Andrés E. Behrens, Jr.
(74) *Attorney, Agent, or Firm* — Novick, Kim & Lee, PLLC; Jae Youn Kim

(57) ABSTRACT

The present invention relates to a method of manufacturing a hyaluronate film and a hyaluronate film manufactured thereby, and more particularly to a method of manufacturing a hyaluronate film through a solvent-casting process or using an automatic film applicator that facilitates mass production and to a hyaluronate film manufactured thereby, which is useful as a mask pack for cosmetics, a patch for medicaments and medical devices, a film-type adhesion inhibitor, etc. Unlike conventional liquid products, the hyaluronate film according to the present invention has a dry surface and
(Continued)

thus entails no concern about microbial contamination, is easy to produce/manage/distribute/use, and has superior mechanical properties, whereby it can be utilized for various applications such as packs, patches, artificial skin and the like for cosmetics, medicaments, and medical devices.

2 Claims, 3 Drawing Sheets

(51) Int. Cl.
*C08L 5/08* (2006.01)
*B29D 7/01* (2006.01)
*B29C 39/00* (2006.01)
*C08J 3/14* (2006.01)

(52) U.S. Cl.
CPC .......... *B29C 2791/005* (2013.01); *B29D 7/01* (2013.01); *B29K 2005/00* (2013.01)

(56) References Cited

FOREIGN PATENT DOCUMENTS

| EP | 2644623 | A1 | 10/2013 | | |
|---|---|---|---|---|---|
| EP | 2910238 | A1 | 8/2015 | | |
| JP | 2009-221391 | A | 10/2009 | | |
| JP | 2009-254756 | A | 11/2009 | | |
| JP | 2014114255 | | * 12/2012 | | |
| JP | 2014114355 | | * 12/2012 | | |
| JP | 2014-114355 | A | 6/2014 | | |
| KR | 10-2009-0012439 | A | 2/2009 | | |
| KR | 10-2013-0045710 | A | 5/2013 | | |
| KR | 10-1615668 | B1 | 4/2016 | | |
| KR | 20190082506 | A | 7/2019 | | |
| WO | 9702845 | A1 | 1/1997 | | |
| WO | 2014093489 | A2 | 6/2014 | | |
| WO | 2015-171483 | A1 | 11/2015 | | |
| WO | WO-2015171483 | A1 * | 11/2015 | ............ | C08G 18/73 |
| WO | 2017126143 | A1 | 7/2017 | | |

OTHER PUBLICATIONS

Updated Translation: JP2014114355A (Yasuyuki) Dec. 2012 (online machine translation), [Retrieved on Jun. 29, 2021]. Retrieved from: Espacenet (Year: 2012).*
Fuchs, John. "Drying: The Effect of Temperature on Relative Humidity." CTG Technical Blog, May 2, 2013, techblog.ctgclean. com/2013/05/drying-the-effect-of-temperature-on-relative-humidity/. (Year: 2013).*
Polymer Science Learning Center I. Molecular Weight, Polymer Science Learning Center, Mar. 1, 2016, web.archive.org/web/20160301145807/pslc.ws/macrog/weight.htm. (Year: 2016).*
JP-2014114255 (Takeyama) Dec. 2012 (online machine translation), [Retrieved on Jun. 29, 2021]. Retrieved from: Espacenet (Year: 2012).*
Jouon, N. et al., "Hydration of Hyaluronic Acid as a Function of the Counterion Type and Relative Humidity", Carbohydrate Polumers, 1995, vol. 26, pp. 69-73.

* cited by examiner

METHOD FOR MANUFACTURING HYALURONATE FILM, AND HYALURONATE FILM MANUFACTURED THEREBY

TECHNICAL FIELD

The present invention relates to a method of manufacturing a hyaluronate film and a hyaluronate film manufactured thereby, and more particularly to a method of manufacturing a hyaluronate film through a solvent-casting process or using an automatic film applicator that facilitates mass production and to a hyaluronate film manufactured thereby, which is useful as a mask pack for cosmetics, a patch for medicaments and medical devices, a film-type adhesion inhibitor, etc.

BACKGROUND ART

Hyaluronate (sodium hyaluronate, hyaluronic acid) is a mucopolysaccharide present in the dermal layer, and is a biopolymer material configured such that disaccharides composed of N-acetyl-D-glucosamine and D-glucuronic acid linked through $\beta$-1,4-glucoside bonds are linked by $\beta$-1,3-glucoside bonds in order to form a hyaluronate chain.

Hyaluronate, which is a white powder, becomes a transparent liquid when dissolved in water, has high water retention capacity due to the large number of hydroxyl groups (—OH) in the molecule thereof, and exhibits high viscoelasticity because of the very large molecular weight of about 0.5 to 3.0 MDa.

Moreover, hyaluronate is distributed evenly in the connective tissue, epithelial and neural tissues of the human body, and has been proven to be effective in regenerating and moisturizing skin, maintaining elasticity and reducing wrinkles, and is thus a biocompatible material having various physiological activities. Recently, the demand for anti-aging-related cosmetics, food, medicaments, and fillers for medical devices, containing hyaluronate, has rapidly increased.

A hyaluronate powder product having minimum water content is configured such that the intramolecular chain is very rigidly connected, so it is less sensitive to microorganisms or changes in the external environment and is thus very stable. However, when the water content of the hyaluronate powder increases, the intramolecular chain becomes flexible, which promotes microbial contamination and changes in properties due to a reduction in molecular weight, resulting in a drastic drop in stability.

Most currently commercially available hyaluronate products are provided in the form of a liquid and contain an excess of water, and thus, the products must be manufactured in sterile facilities due to the concern of microbial contamination, or preservatives must be used due to the concern about safety, making it difficult to expand industrial uses thereof in terms of adoptability and safety.

Particularly, in the case of joint injections or fillers containing hyaluronate as a main ingredient, the amount of hyaluronate in the product is low, about 1 to 3%, and about 97 to 99% thereof is water, and thus the product is rapidly decomposed when introduced into the body and thus requires frequent administration. Furthermore, since these products are very viscous, the introduction thereof to the skin in the form of an injection may generate pain in the patient due to high pressure, and may cause discomfort in the form of bruising of the treatment area.

U.S. Pat. No. 6,630,167 discloses a gel-type adhesion inhibitor using hyaluronate and a toxic crosslinking agent, and Korean Patent Application Publication No. 2009-0012439 discloses a hyaluronic-acid/carboxymethyl-cellulose composite derivative film in a mixed form of an N-acyl urea pendant type and an auto-crosslinked type, derived by reacting a crosslinking activator and a crosslinking adjuvant on the surface of a hyaluronic-acid/carboxymethyl-cellulose composite film, and a method of manufacturing the same. However, since the above patents do not completely remove the toxic crosslinking agent and the like after gel preparation, there is a concern of side effects thereof.

As described above, the demand for hyaluronate having a variety of physiological activities is increasing, but there is no research on hyaluronate films so far.

Therefore, the present inventors have endeavored to manufacture hyaluronate films for use in various applications and have ascertained that a hyaluronate film may be manufactured through a casting process using an automatic film applicator or a solvent-casting process, thus culminating in the present invention.

DISCLOSURE

Technical Problem

An objective of the present invention is to provide a method of manufacturing a hyaluronate film, which has biocompatibility and an anti-aging function and is thus useful in a variety of fields.

Another objective of the present invention is to provide a hyaluronate film containing hyaluronate at a high concentration and having a uniform surface and a mass production method thereof.

Still another objective of the present invention is to provide a hyaluronate film having resistance to microorganisms and superior mechanical properties and a mask pack, a patch, artificial skin for medical devices, and an adhesion inhibitor, each including the same.

Technical Solution

In order to accomplish the above objectives, the present invention provides a method of manufacturing a hyaluronate film, the method including (a) preparing a hyaluronate solution by dissolving hyaluronate in a solvent and (b) drying the hyaluronate solution through a solvent-casting process or a casting process using an automatic film applicator.

In the present invention, the solvent-casting process may include (a) preparing a 0.1 to 30 wt % hyaluronate solution by dissolving hyaluronate in a solvent; and (b) placing the hyaluronate solution in a mold and drying the hyaluronate solution under conditions of a relative humidity of 30 to 70% and a drying temperature of 30 to 50° C.

In the present invention, the casting process using the automatic film applicator may include (a) preparing a 0.1 to 30 wt % hyaluronate solution by dissolving hyaluronate in a solvent, (b) placing the hyaluronate solution in an automatic film applicator and casting a film to a thickness of 0.025 to 5 mm and (c) drying the cast film at 30 to 50° C.

In addition, the present invention provides a hyaluronate film manufactured from hyaluronate having a molecular weight of 0.1 to 2.5 MDa and having a tensile strength of 15 to 320 MPa and an elongation of 3 to 68%.

Advantageous Effects

According to the present invention, a method of manufacturing a hyaluronate film facilitates mass production and enables the properties of the film to be easily controlled by adjusting the viscosity of hyaluronate and the thickness of the film.

BEST MODE

Figure 1:
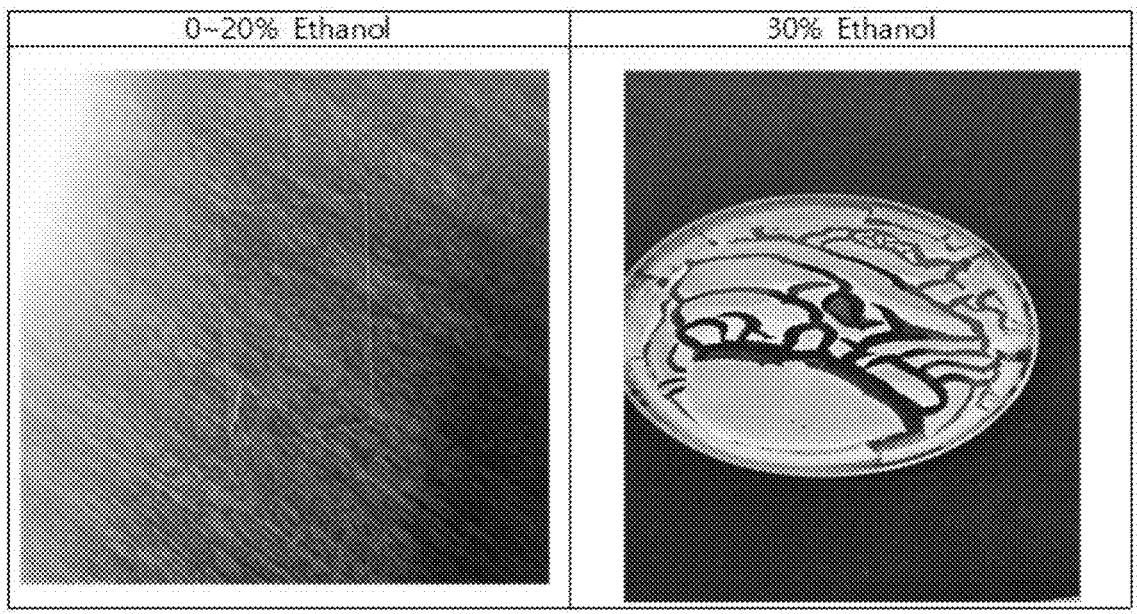
FIG. 1 shows hyaluronate films manufactured through a solvent-casting process depending on the concentration of hyaluronate.
Figure 2:
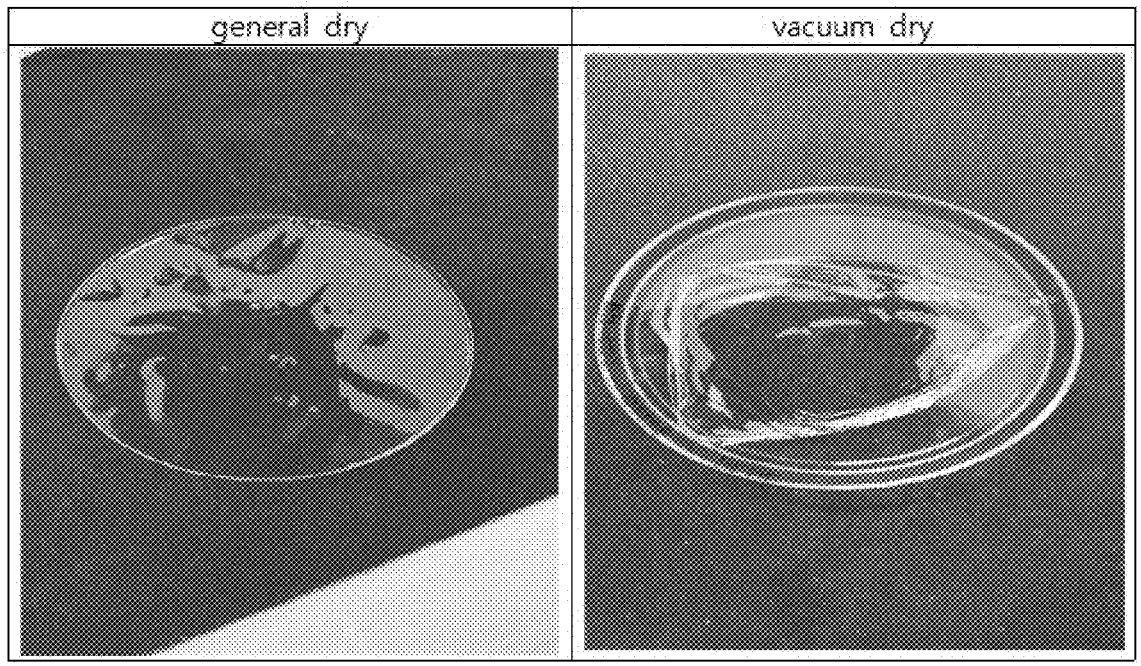
FIG. 2 shows hyaluronate films manufactured through a solvent-casting process depending on the type of drying process.

The present invention is intended to confirm that a hyaluronate film that is capable of solving the problems with conventional liquid hyaluronate products which are easily contaminated by microorganisms during production, storage, distribution and use can be manufactured using a solvent-casting process in which hyaluronate is dissolved in water or in an ethanol aqueous solution and is then dried under specific constant-temperature and constant-humidity conditions.

In an embodiment of the present invention, films were manufactured depending on the molecular weight and concentration of hyaluronate and the drying process, and the mechanical strength and ability to resist microorganisms for commercialization thereof were evaluated.

Consequently, it can be confirmed that when a 0.1 to 30 wt % solution of hyaluronate having a molecular weight of 0.1 to 2.5 MDa is dried at a relative humidity of 30 to 70% and a temperature of 30 to 50° C., a film having a smooth surface and superior mechanical strength and ability to resist microorganisms can be manufactured. Moreover, it can be confirmed that the manufactured hyaluronate film has superior mechanical properties to an extent that it is easily formed into a desired shape with general scissors or a knife, and is superior in stability to water in the work room.

In addition, the present invention is intended to confirm that when a hyaluronate solution is placed in an automatic film applicator and dried, hyaluronate films having various thicknesses can be uniformly mass-produced and it is possible to control the properties thereof by adjusting the viscosity of the hyaluronate solution and the film thickness.

In the present invention, hyaluronate is dissolved in water or an ethanol aqueous solution to afford a 0.1 to 30 wt % hyaluronate solution, which is then placed in an automatic film applicator, followed by film casting at various thicknesses and then drying at 30 to 50° C., thereby manufacturing a hyaluronate film. Consequently, it can be confirmed that when a 0.1 to 30 wt % hyaluronate solution (300 to 100,000 cPs) is cast using an automatic film applicator and is then dried at a temperature of 30 to 50° C., a hyaluronate film having a uniform surface can be mass-produced. Moreover, it can be confirmed that the manufactured hyaluronate film has superior mechanical properties to an extent that it is easily formed into a desired shape with general scissors, a knife or a typical mold.

Therefore, an aspect of the present invention pertains to a method of manufacturing a hyaluronate film, including (a) preparing a hyaluronate solution by dissolving hyaluronate in a solvent and (b) drying the hyaluronate solution through a solvent-casting process or a casting process using an automatic film applicator.

In the present invention, the solvent-casting process includes (a) preparing a 0.1 to 30 wt % hyaluronate solution by dissolving hyaluronate in a solvent and (b) placing the hyaluronate solution in a mold and drying the hyaluronate solution under conditions of a relative humidity of 30 to 70% and a drying temperature of 30 to 50° C.

In the present invention, hyaluronate is configured such that a salt binds to hyaluronic acid, and examples thereof may include, but are not limited to, sodium hyaluronate, calcium hyaluronate, potassium hyaluronate, and the like.

The skin penetration, absorption and mechanical properties of hyaluronate may vary depending on the molecular weight thereof, and the use of hyaluronate having a molecular weight of 0.1 to 2.5 MDa is preferable. If the molecular weight of hyaluronate is less than 0.1 MDa, it is difficult to form a film. On the other hand, if the molecular weight of hyaluronate exceeds 2.5 MDa, the surface of the film may become non-uniform due to the high viscosity thereof.

The solvent is used to dissolve hyaluronate, and includes 100% water or an ethanol aqueous solution, and the ethanol aqueous solution preferably contains 0.01 to 29 vol % of ethanol. When water is used alone to dissolve hyaluronate, much care is required to prevent microbial contamination, but when an ethanol aqueous solution is used to dissolve hyaluronate, an effect of preventing microbial contamination may increase with an increase in the amount of ethanol, and moreover, the film formation time may be reduced. However, if the amount of ethanol is 30 vol % or more, the film may become opaque or may not be formed with an increase in the molecular weight of hyaluronate.

In the solvent-casting process according to the present invention, the concentration of the hyaluronate solution is preferably 0.1 to 30 wt %. If the concentration of the hyaluronate solution is less than 0.1 wt %, it is difficult to form a film. On the other hand, if the concentration thereof exceeds 30 wt %, the surface of the film may become irregular due to the high viscosity thereof.

In the present invention, the hyaluronate solution for manufacturing a hyaluronate film is placed in a mold and dried at a relative humidity of 30 to 70% and a drying temperature of 30 to 50° C. for 6 to 12 hr.

Any mold may be used without particular limitation, so long as it is capable of accommodating the hyaluronate solution, and for example, a mold made of acryl, glass or stainless steel (SUS) may be used.

In the solvent-casting process according to the present invention, the drying may be performed without particular limitation, so long as it satisfies the above conditions of relative humidity and drying temperature, and the drying is preferably conducted in a constant-temperature and constant-humidity chamber. If the relative humidity or drying temperature falls out of the above range, a film may not be formed, or a film having a non-uniform surface may be formed.

The drying time may be appropriately adjusted within the above range depending on the concentration of the hyaluronate solution and the size of the mold.

In the present invention, the solvent-casting process is widely used for film formation, and is performed in a manner in which an organic material is completely dissolved in a solvent and is then solidified by evaporating the solvent.

The hyaluronate film manufactured through the solvent-casting process exhibits superior tensile strength and elongation. For example, when the molecular weight of hyaluronate is 0.1 to 2.5 MDa, the resulting film may exhibit a tensile strength of about 30 to 320.0 MPa and an elongation of about 12 to 68%, and thus is free of microbial contamination and is easy to manage and use and may thus be variously utilized, unlike conventional liquid hyaluronate products.

The hyaluronate film manufactured according to the present invention has a water content of 5 to 20 wt %. If the water content is less than 5 wt %, the surface thereof hardens and breaks or use thereof is inconvenient. On the other hand, if the water content exceeds 20 wt %, the shape of the film cannot be maintained.

Also, the hyaluronate film manufactured according to the present invention has a thickness of 0.025 to 5 mm, a uniform surface, and a transparent color. The end use of the hyaluronate film may vary depending on the thickness thereof. When components other than hyaluronate are contained, a film having a thickness of 0.025 to 5 mm cannot be manufactured. However, the hyaluronate film of the present invention contains 10 to 100 wt % of hyaluronate, among components other than water, and thus may have a thickness of 0.025 to 5 mm.

The hyaluronate film may be utilized as a mask pack for cosmetics, a patch, an adhesion inhibitor for medical devices, etc.

For reference, adhesion usually occurs during healing of inflammation, and means that granulation tissue or scars that are formed are combined, or fibrin, which is precipitated in a large amount, becomes entangled. In general, the incidence of adhesion after laparotomy is about 67 to 93%, some of which spontaneously separates. In most cases, adhesion is present even after wound healing, thus causing various kinds of sequelae. Therefore, an adhesion inhibitor is used to cover the wound after surgery or to physically and chemically block the occurrence of adhesion of surrounding tissues by pharmacological action, etc.

Meanwhile, in the present invention, the casting process using the automatic film applicator includes (a) preparing a 0.1 to 30 wt % hyaluronate solution by dissolving hyaluronate in a solvent, (b) placing the hyaluronate solution in an automatic film applicator and casting a film to a thickness of 0.025 to 5 mm, and (c) drying the cast film at 30 to 50° C.

In the present invention, hyaluronate is configured such that a salt binds to hyaluronic acid, and examples thereof may include, but are not limited to, sodium hyaluronate, calcium hyaluronate, potassium hyaluronate, and the like.

In the casting process using the automatic film applicator according to the present invention, the molecular weight of hyaluronate is not particularly limited, and is preferably 0.1 to 2.5 MDa. Furthermore, the amount of hyaluronate in the hyaluronate solution is 0.1 to 30 wt %. If the concentration of the hyaluronate solution is less than 0.1 wt %, it is difficult to form a film. On the other hand, if the concentration thereof exceeds 30 wt %, the surface of the film may become irregular due to the high viscosity thereof. For reference, the viscosity of the hyaluronate solution within the above concentration and molecular weight ranges is 300 to 100,000 cPs. Hyaluronic acid having a low molecular weight has to be dissolved at a high concentration to satisfy the above reference viscosity, whereas hyaluronic acid having a high molecular weight has to be dissolved at a low concentration to satisfy the above reference viscosity, thereby manufacturing a uniform film.

The kind and amount of the solvent used to dissolve hyaluronate are as described above.

The casting process is preferably performed at a constant rate of 5 to 20 mm/s.

Figure 3:
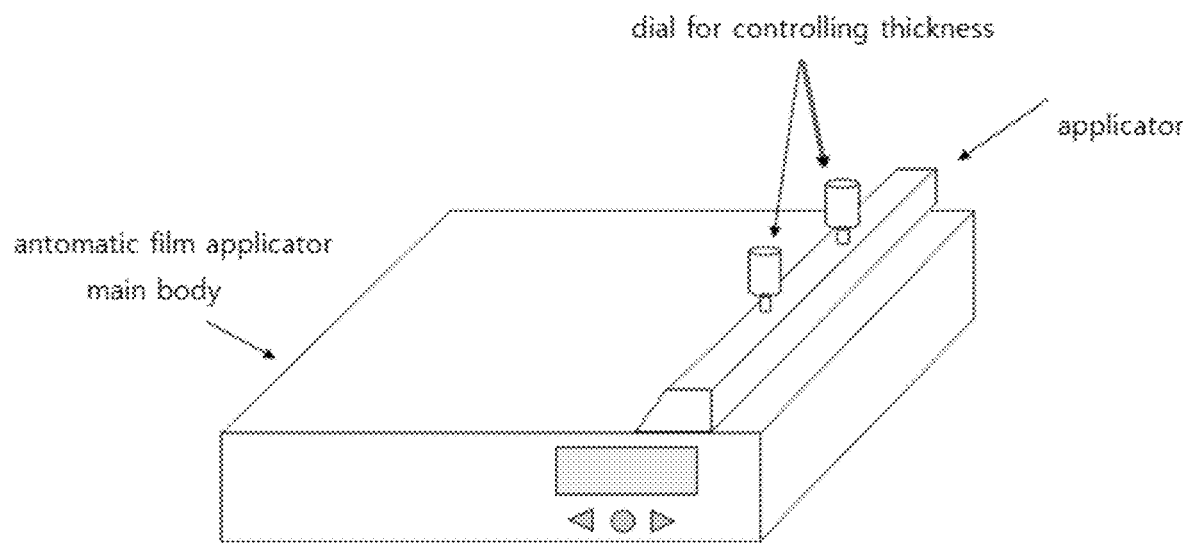
FIG. 3 shows a typical automatic film applicator.

In the present invention, the automatic film applicator is widely used to manufacture a typical film, and includes a main body, an applicator for adjusting film thickness, and a thickness control dial, as shown in FIG. 3.

In the present invention, the thickness of the hyaluronate film is preferably 0.025 to 5 mm. If the thickness of the hyaluronate film is less than 0.025 mm, it is difficult to form a film. On the other hand, if the thickness thereof exceeds 5 mm, flow becomes large with an increase in the film thickness, undesirably causing surface wrinkles and requiring a long drying time.

In the present invention, the cast film is preferably dried at 30 to 50° C. for 6 to 24 hr. Here, the drying process may be variously performed without particular limitation, so long as the drying is conducted at 30 to 50° C.

For reference, when the hyaluronate film is dried through the solvent-casting process, the film is formed under constant-temperature and constant-humidity drying conditions, but is not formed under convection drying conditions.

The drying time may be appropriately controlled within the above range by adjusting the concentration of the hyaluronate solution and the applicator in the automatic film applicator.

The hyaluronate film is manufactured from hyaluronate having a molecular weight of 0.1 to 2.5 MDa through the casting process using the automatic film applicator and has a tensile strength of 30 to 320 MPa and an elongation of 12 to 68%, and the properties of the hyaluronate film may be controlled by adjusting the viscosity of the hyaluronate solution and the film thickness.

The hyaluronate film manufactured according to the present invention has a water content of 5 to 20 wt %. If the water content is less than 5 wt %, the surface of the film hardens and breaks or use thereof is inconvenient. On the other hand, if the water content exceeds 20 wt %, the shape of the film cannot be maintained.

The hyaluronate film may be utilized as a mask pack for cosmetics, a patch, artificial skin for medical devices, an adhesion inhibitor, etc.

MODE FOR INVENTION

A better understanding of the present invention will be given through the following examples. However, these examples are merely set forth to illustrate the present invention but are not to be construed as limiting the scope of the present invention, as will be apparent to those skilled in the art.

EXAMPLE 1

Manufacture of Hyaluronate Film Through Solvent Casting 1-1: Evaluation of Film Formation Ability Depending on Changes in Molecular Weight In order to evaluate film formation ability depending on the molecular weight of hyaluronate, each of four kinds of sodium hyaluronate having molecular weights of 0.1 MDa, 0.8 MDa, 1.2 MDa, and 2.5 MDa (Hyaluronate (Hi-Aqua™), available from JinWoo Bio) was dissolved at a concentration of 0.5 to 10.0 wt % in a 20 vol % ethanol aqueous solution, placed in an acryl mold, and then dried for 6 to 24 hr in a constant-temperature and constant-humidity oven (at a relative humidity of 50% and a temperature of 40° C.), thereby manufacturing a hyaluronate film.

Consequently, it was confirmed that when the molecular weight of hyaluronate was 0.8, 1.2 and 2.5 MDa, a film was well formed at a hyaluronate concentration of 0.5% or more, but hyaluronate having a molecular weight of 0.1 MDa was capable of forming a film when dissolved at a concentration of 5% or more.

Based on the results of measurement of the water content of the manufactured hyaluronate film using a water content meter, the 0.1 MDa film was found to have a water content of 11 wt %, the 0.8 MDa film was found to have a water content of 13 wt %, the 1.2 MDa film was found to have a water content of 15 wt %, and the 2.5 MDa film was found to have a water content of 30 wt %. Due to the high water content of hyaluronic acid (HA) itself, it was impossible to manufacture a film having a water content less than 10%, and the water content in the film was determined to be about 10 to 30% depending on the molecular weight of hyaluronate.

1-2: Evaluation of Film Formation Ability Depending on Solvent Conditions

In order to evaluate film formation ability depending on the solvent conditions, sodium hyaluronate having a molecular weight of 1.2 MDa was dissolved at a concentration of 1.0 wt % in a 0 to 30 vol % ethanol aqueous solution, placed in an acryl mold, and then dried for 12 hr in a constant-temperature and constant-humidity oven (at a relative humidity of 50% and a temperature of 40° C.), thereby manufacturing a hyaluronate film.

Consequently, it was confirmed that when the concentration of ethanol in the ethanol aqueous solution was 0 to 20 vol %, a transparent film was well formed, whereas when the concentration of ethanol was 30 vol %, hyaluronate was not well dissolved, and thus the film was not well formed (FIG. 1).

Moreover, when the film was manufactured using 100% water alone, an opaque film was formed due to intermittent microbial contamination. On the other hand, when the ethanol content was 5% or more, almost no microbial contamination occurred during the film formation process.

The higher the concentration of ethanol in the ethanol aqueous solution, the faster the film was formed. When purified water was used alone as the solvent, a drying time of about 24 hr was required, but it was possible to form a film within 12 hr when using the ethanol aqueous solution.

1-3: Evaluation of Film Formation Ability Depending on Drying Conditions

In order to evaluate film formation ability depending on the drying conditions, sodium hyaluronate having a molecular weight of 1.2 MDa was dissolved at a concentration of 1.0 wt % in a 20 vol % ethanol aqueous solution, placed in an acryl mold and then dried for 12 hr or more in a constant-temperature and constant-humidity oven (at a relative humidity of 50 to 90% and a temperature of 30 to 60° C.), thereby manufacturing a hyaluronate film.

Consequently, it was confirmed that the film was not formed even when dried for 24 hr or more at a relative humidity of 80% or more, and that the film was formed within a faster time (12 hr to 24 hr) as the temperature was elevated from 30° C. to 40° C.

For reference, in the case of hyaluronate, it is preferable to perform drying at 50° C. or lower because the molecular weight of hyaluronate may decrease and thus mechanical properties may deteriorate when hyaluronate is allowed to stand at a temperature of 50° C. or higher for a long time.

COMPARATIVE EXAMPLE 1

Evaluation of Film Formation Ability Using Convection Oven

A hyaluronate film was manufactured in the same manner as in Example 1-3, with the exception that typical drying was performed at 40° C. for 12 hr or more using a convection oven in lieu of the constant-temperature and constant-humidity oven. Based on the results of evaluation of the shape of the manufactured film, it was confirmed that the film had a wrinkled surface and contained bubbles in portions thereof.

COMPARATIVE EXAMPLE 2

Evaluation of Film Formation Ability Using Vacuum Oven

A hyaluronate film was manufactured in the same manner as in Example 1-3, with the exception that drying was performed at 40° C. for 12 hr or more using a vacuum oven (~0.05 mbar) in lieu of the constant-temperature and constant-humidity oven. Based on the results of evaluation of the shape of the manufactured film, it was confirmed that the film had a wrinkled surface and that both ends thereof were curled.

TEST EXAMPLE 1

Measurement of Mechanical Properties of Hyaluronate Film

Sodium hyaluronate having molecular weights of 0.8 MDa, 1.2 MDa and 2.5 MDa (Hyaluronate (Hi-Aqua™), available from JinWoo Bio) was dissolved at a concentration of 1.0 wt % in a 20 vol % ethanol aqueous solution, and hyaluronate having a molecular weight of 0.1 MDa was dissolved at a concentration of 5 wt % therein, and each solution was placed in an acryl mold and then dried for 12 hr in a constant-temperature and constant-humidity oven (at a relative humidity of 50% and a temperature of 40° C.), thereby manufacturing a hyaluronate film.

In order to measure the mechanical properties of the manufactured hyaluronate film, the film was cut to a size of 3 cm×5 cm using a TA-XT2i texture analyzer (Stable Micro System, UK), and was then mounted on tensile grips, after which the tensile strength and elongation thereof were measured. The results are shown in Table 1 below.

TABLE 1

| | Molecular weight of hyaluronate | | | |
| --- | --- | --- | --- | --- |
| | 0.1 MDa | 0.8 MDa | 1.2 MDa | 2.5 MDa |
| Tensile Strength | 15.1 | 111.1 | 151.5 | 300.0 |
| Elongation (%) | 3 | 35 | 45.5 | 65.0 |

As is apparent from Table 1, the hyaluronate film having a molecular weight of 0.1 MDa exhibited a tensile strength of 15.1 MPa and an elongation of 3%, the hyaluronate film having a molecular weight of 0.8 MDa exhibited a tensile strength of 111.1 MPa and an elongation of 35%, the hyaluronate film having a molecular weight of 1.2 MDa exhibited a tensile strength of 151.5 MPa and an elongation of 45.5%, and the hyaluronate film having a molecular weight of 2.5 MDa exhibited a tensile strength of 300.0 MPa and an elongation of 65.0%. The manufactured hyaluronate film manifested superior mechanical properties, and both the tensile strength and the elongation thereof were increased with an increase in the molecular weight thereof.

TEST EXAMPLE 2

Measurement of Ability of Hyaluronate Film to Resist Microorganisms

The total count of bacteria refers to the number of bacteria that grow on a plate count agar among the bacteria present in a sample. In order to evaluate the ability of the hyaluronate film to resist contamination with microorganisms, the sample and the plate count agar were mixed and solidified in a Petri dish and cultured, after which the viable count in the sample was calculated based on the number of colonies of bacteria that formed.

(1) Preparation of Solution and Reagent

Plate Count Agar 5.0 g of tryptone, 2.5 g of a yeast extract, 1.0 g of dextrose and 15.0 g of agar were added with distilled water such that the total volume was 1,000 ml, and the resulting solution was adjusted to a pH of 7.0±0.2 and then sterilized at 121° C. for 15 min.

Sterile Saline Solution

A 0.9% sodium chloride aqueous solution was sterilized at 121° C. for 15 min and used as a sterile saline solution.

(2) Test Method

A liquid product obtained by dissolving each of a hyaluronate solid film having a molecular weight of 1.2 MDa manufactured in Test Example 1 and hyaluronate having a molecular weight of 1.2 MDa at 1 vol % in typical purified water was allowed to stand in a general laboratory for 15 days.

Next, 0.5 g of each of the hyaluronate film and the hyaluronate solution was dissolved in 50 ml of the sterile saline solution, placed in 250 ml of the sterilized plate count agar at 43 to 45° C., and shaken.

Before solidifying the medium, the mixed solution was placed in a Petri dish, followed by cooling solidification and culture at 35±1° C. for 24 to 48 hr. The number of colonies generated after culturing was measured and divided by 0.5 g to determine the total count of bacteria. The results are shown in Table 2 below.

TABLE 2

| | Before air exposure | | After air exposure | |
| --- | --- | --- | --- | --- |
| | Hyaluronate solution | Hyaluronate film | Hyaluronate solution | Hyaluronate film |
| Microbial count (cfu/g) | 0 | 0 | 1,500 to 5,000 | 0 to 8 |

As is apparent from Table 2, after air exposure for 15 days, the microbial count was about 1,500 to 5,000 cfu in the 1% hyaluronate solution, but in the case of the hyaluronate film, the microbial count was about 0 to 8 cfu, indicative of almost no changes before and after exposure.

EXAMPLE 2

Manufacture of Hyaluronate Film Through Casting Using Automatic Film Applicator 2-1: Evaluation of Film Formation Ability Depending on Changes in Molecular Weight In order to evaluate film formation ability depending on the molecular weight of hyaluronate, each of five kinds of sodium hyaluronate having molecular weights of 0.1 MDa, 0.8 MDa, 1.2 MDa, 1.5 MDa and 2.5 MDa (Hi-Aqua™) (available from JinWoo Bio) was dissolved at a concentration of 0.1 to 30 wt % in a 20 vol % ethanol aqueous solution, and was then processed so as to have a viscosity of less than 300 cPs (low viscosity), 300 to 100,000 cPs (optimal viscosity) and greater than 100,000 cPs (high viscosity), followed by film casting to a thickness of 0.025 to 5 mm by adjusting the applicator of an automatic film applicator (COAD 411, Uiwang Machinery, Korea) and then drying for 6 to 24 hr in a constant-temperature and constant-humidity oven (at a relative humidity of 50% and a temperature of 40° C.), thereby manufacturing a hyaluronate film. The state of the film depending on the viscosity is shown in FIG. 4.

For reference, the viscosity of hyaluronate for manufacturing a film using an automatic film applicator was measured under the following conditions.

Measurement instrument: Brookfield RV-II viscometer (Spindle No. 7, 12 rpm, 25° C.)

Figure 4:
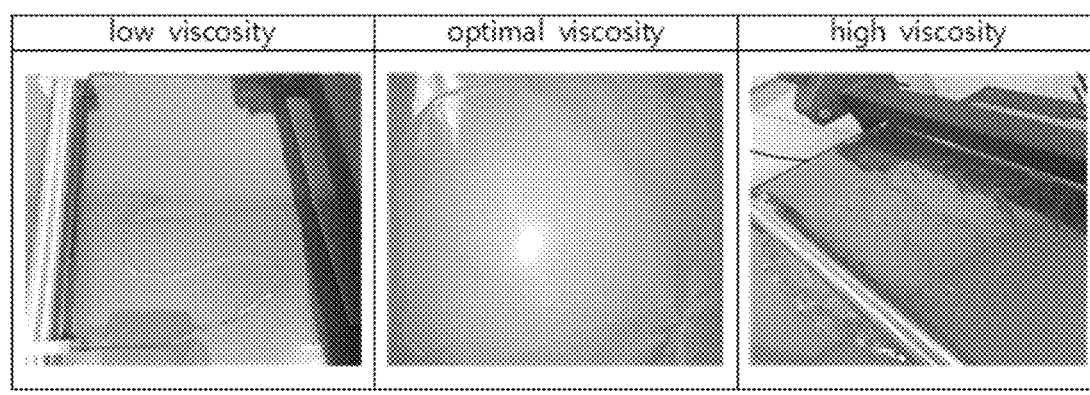
FIG. 4 shows hyaluronate films manufactured through a casting process using an automatic film applicator depending on the viscosity of hyaluronate.

As shown in FIG. 4, regardless of the molecular weight of hyaluronate, when the viscosity of the hyaluronate solution was less than 300 cPs (low viscosity), the film was not formed. When the viscosity thereof was 300 to 100,000 cPs (optimal viscosity), it was possible to manufacture a film having a uniform surface using an automatic film applicator, but when the viscosity was greater than 100,000 cPs (high viscosity), an uneven appearance resulted due to surface entanglement, making it impossible to form a film.

2-2: Evaluation of Film Formation Ability Depending on Drying Conditions

In order to evaluate film formation ability depending on the drying conditions, sodium hyaluronate having a molecular weight of 1.2 MDa was dissolved at a concentration of 2.0 wt % in a 10 vol % ethanol aqueous solution, cast to a film thickness of 0.1 mm using the applicator in an automatic film applicator, and dried for 6 to 24 hr in a constant-temperature and constant-humidity oven (at a relative humidity of 50 to 90% and a temperature of 30 to 60° C.) and a convection oven (at a temperature of 30 to 60° C.), thereby manufacturing a hyaluronate film, and the state of the film depending on the drying conditions was evaluated.

Consequently, it was confirmed that the surface of the hyaluronate film manufactured using the automatic film applicator was formed very uniformly not only in the constant-temperature and constant-humidity oven but also in the convection oven.

Moreover, the drying time was 12 hr or more shorter in the convection oven than in the constant-temperature and constant-humidity oven, indicating that the hyaluronate film can be produced more quickly.

COMPARATIVE EXAMPLE 3

Evaluation of Film Formation Ability Depending on Viscosity of Hyaluronate Solution In order to evaluate film formation ability through film casting depending on the viscosity of the hyaluronate solution, sodium hyaluronate having a molecular weight of 0.1 to 2.5 MDa (Hi-Aqua™) (available from JinWoo Bio) was dissolved at a concentration of 0.1 to 30 wt % in a 10 vol % ethanol aqueous solution, cast to a film thickness of 0.1 mm using the applicator of an automatic film applicator, and dried for 24 hr or more in a constant-temperature and constant-humidity oven (at a relative humidity of 50% and a temperature of 50° C.), thereby manufacturing a hyaluronate film, and the state of the film depending on the viscosity was evaluated.

Consequently, regardless of the molecular weight of hyaluronate, when the viscosity of the hyaluronate solution was less than 300 cPs (low viscosity), it was impossible to form a film, and when the viscosity thereof was greater than 100,000 cPs (high viscosity), it was impossible to form a film having a uniform surface due to the excessive viscosity, but it was confirmed that a film having a uniform surface was formed upon drying at an optimal viscosity.

COMPARATIVE EXAMPLE 4

Evaluation of Film Formation Ability Depending on Film Thickness

In order to evaluate hyaluronate film formation ability depending on the thickness using the applicator of an automatic film applicator, sodium hyaluronate having a molecular weight of 1.2 MDa was dissolved at a concentration of 2.0 wt % in a 10 vol % ethanol aqueous solution, cast to a film thickness of 0.024 to 5.001 mm using a film applicator, and dried for 24 hr or more in a constant-temperature and constant-humidity oven (at a relative humidity of 50% and a temperature of 50° C.), thereby manufacturing a hyaluronate film, and the state of the film depending on the drying conditions was evaluated.

Figure 5:
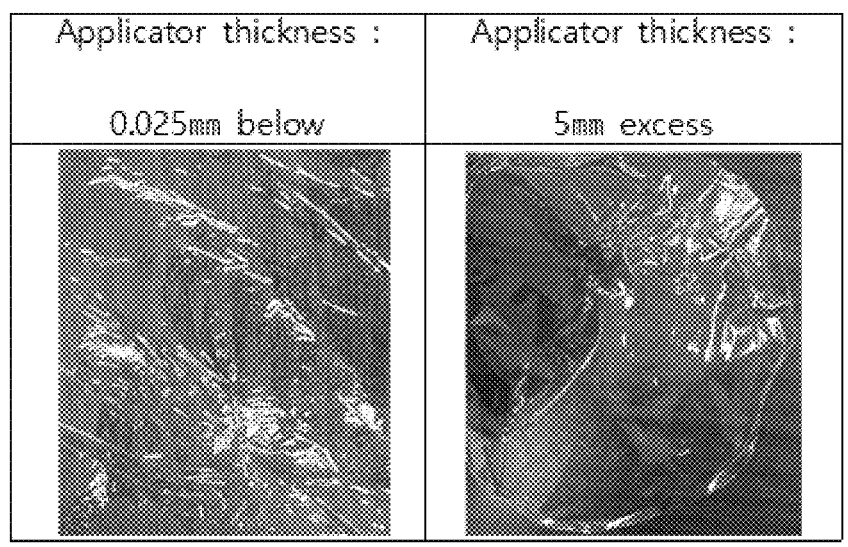
FIG. 5 shows hyaluronate films manufactured through a casting process using an automatic film applicator depending on the applicator thickness.

As shown in FIG. 5, when the film thickness was less than 0.025 mm, the film had an uneven surface and was thus difficult to use, and when the film thickness exceeded 5 mm, the film was cast in a state in which molding was impossible, and even after molding, the film surface was not uniform and the drying time was also long, making it unsuitable for forming a film.

TEST EXAMPLE 3

Measurement of Mechanical Properties of Hyaluronate Film

In order to measure the mechanical properties of the hyaluronate film manufactured in Example 2-1, the manufactured film (thickness: 1 mm) was cut to a size of 3 cm×5 cm using a TA-XT2i texture analyzer (Stable Micro System, UK) and was then mounted on tensile grips, after which the tensile strength and elongation thereof were measured. The results are shown in Table 3 below.

TABLE 3

|  | Molecular weight of hyaluronate solution (MDa) | | | | |
| --- | --- | --- | --- | --- | --- |
|  | 0.1 | 0.8 | 1.2 | 1.5 | 2.5 |
| Tensile Strength | 30 to 35 | 120 to 130 | 151 to 170 | 210 to 240 | 300 to 321 |
| Elongation (%) | 12 to 15 | 25 to 33 | 45 to 50 | 55 to 58 | 65 to 68 |

Based on the results of measurement of the mechanical properties of the hyaluronate film, the mechanical properties were found to be affected by molecular weight of hyaluronate, but not by the concentration of hyaluronate or the viscosity of the hyaluronate solution.

As is apparent from Table 3, as the molecular weight of hyaluronate was higher, tensile strength was increased from 30 to 321 MPa and elongation was increased from 12% to 68%.

TEST EXAMPLE 4

Measurement of Water Content of Hyaluronate Film

In order to measure the water content of the hyaluronate film manufactured in Example 2-1, the water content of the manufactured film (thickness: 1 mm) was measured using a water content meter. The results are shown in Table 4 below.

TABLE 4

|  | Molecular weight of hyaluronate solution (MDa) | | | | |
| --- | --- | --- | --- | --- | --- |
|  | 0.1 | 0.8 | 1.2 | 1.5 | 2.5 |
| Water content (%) | 12 | 13 | 15 | 25 | 30 |

As is apparent from Table 4, the water content of the manufactured hyaluronate film was measured to be 12 to 30 wt % using a water content meter. As in the film realized through solvent casting of Example 1-3, it was impossible to manufacture a film having a water content less than 10% due to the high water content of HA itself, and the water content in the film was determined to be about 10 to 30 wt % depending on the molecular weight of hyaluronate.

While specific portions of the present invention have been described in detail, it will be understood by those skilled in the art that this specific technology is only a preferred embodiment, and that the scope of the present invention is not limited thereby. Therefore, the actual scope of the present invention will be defined by the appended claims and their equivalents.

INDUSTRIAL APPLICABILITY

Unlike conventional liquid products, the hyaluronate film according to the present invention has a dry surface, and thus entails no concern about microbial contamination, is easy to produce/manage/distribute/use and has superior mechanical properties, whereby it can be utilized for various applications such as packs, patches, artificial skin and the like for cosmetics, medicaments, and medical devices.

The invention claimed is:

1. A method of manufacturing a hyaluronate film through a solvent-casting process, the method comprising:
   (a) preparing a 0.1 to 30 wt % hyaluronate solution by dissolving hyaluronate having a molecular weight of 0.1 to 2.5 MDa in a 5 to 29 vol % ethanol aqueous solution; and
   (b) placing the hyaluronate solution in a mold and drying the hyaluronate solution using a constant-temperature and constant-humidity chamber under conditions of a relative humidity of 30 to 70% and a drying temperature of 30 to 50° C.

2. A method of manufacturing a hyaluronate film using an automatic film applicator, the method comprising:
   (a) preparing a hyaluronate solution having a viscosity of 300 to 100,000 cPs at 25° C. and containing 0.1 to 30 wt % hyaluronate by dissolving the hyaluronate in a 5 to 29 vol % ethanol aqueous solution;
(b) placing the hyaluronate solution in an automatic film applicator and casting a film to a thickness of 0.025 to 5 mm; and
(c) drying the cast film at 30 to 50° C.

\* \* \* \* \*